(12) United States Patent
Backes et al.

(10) Patent No.: US 7,598,404 B2
(45) Date of Patent: Oct. 6, 2009

(54) PROCESS FOR THE PRODUCTION OF ETHERS

(75) Inventors: Adrian Francis Backes, London (GB); Andrew George Hiles, London (GB); David Mark Sutton, London (GB)

(73) Assignee: Davy Process Technology Limited, London (GB)

( * ) Notice: Subject to any disclaimer, the term of this patent is extended or adjusted under 35 U.S.C. 154(b) by 0 days.

(21) Appl. No.: 10/582,370

(22) PCT Filed: Dec. 1, 2004

(86) PCT No.: PCT/GB2004/005054

§ 371 (c)(1),
(2), (4) Date: Sep. 11, 2006

(87) PCT Pub. No.: WO2005/058855

PCT Pub. Date: Jun. 30, 2005

(65) Prior Publication Data

US 2007/0088169 A1     Apr. 19, 2007

(30) Foreign Application Priority Data

Dec. 16, 2003   (GB) ................... 0329152.3

(51) Int. Cl.
*C07D 307/08* (2006.01)
(52) U.S. Cl. .................................... 549/508
(58) Field of Classification Search ............... 549/508; 546/508
See application file for complete search history.

(56) References Cited

U.S. PATENT DOCUMENTS 6,936,727 B2 * 8/2005 Sutton et al. ............... 549/508

FOREIGN PATENT DOCUMENTS

| EP | 1108702 A1 | 6/2001 |
|---|---|---|
| WO | WO 86/03189 A1 | 6/1986 |
| WO | WO 99/35113 A2 | 7/1999 |
| WO | 03006446 A1 | 1/2003 |

OTHER PUBLICATIONS

International Search Report for International Application PCT/GB2004/005054, dated Feb. 22, 2005, 4 pages.

* cited by examiner

*Primary Examiner*—D. Margaret Seaman
*Assistant Examiner*—Nizal S Chandrakumar
(74) *Attorney, Agent, or Firm*—Senniger Powers LLP

(57) ABSTRACT

A process for the production of an ether optionally with a diol and/or a lactone, by reaction of a corresponding organic feed material selected from unsaturated dicarboxylic acids and/or anhydrides, mono-esters of unsaturated dicarboxylic acids and/or anhydrides, diesters of unsaturated dicarboxylic acids and/or anhydrides, unsaturated lactones, and mixtures of two or more thereof in the presence of hydrogen which comprises the steps of-(a) supplying a stream comprising at least a portion of the organic feed material to a pre-reactor zone comprising catalyst and operating under reaction conditions and contacting said feed with a hydrogen containing stream such that at least some of the carbon carbon double bonds are saturated; (b) vaporising the at least partly saturated feed into the hydrogen containing stream in a vaporizing zone; (c) supplying the hydrogen-containing stream containing the vaporized at least partially saturated feed to a reaction zone comprising catalyst and operating under reaction conditions; (d) recovering from the reaction zone a product stream comprising the ether and optionally diol and/or lactone; and (e)recycling depleted hydrogen-containing stream to at least the pre-reactor zone or the vaporization zone.

21 Claims, 2 Drawing Sheets

PROCESS FOR THE PRODUCTION OF ETHERS

The present invention relates to a process for the production of ethers optionally with the co-production of diols and/or lactones which includes hydrogenation of an organic feed material comprising one or more compounds having a carbon carbon double bond. In particular, it relates to the production of ethers optionally with the co-production of diols and/or the corresponding lactones by the reaction of a feed material comprising unsaturated dicarboxylic acids and/or anhydrides, mono-esters of unsaturated dicarboxylic acids and/or anhydrides, diesters of unsaturated dicarboxylic acids and/or anhydrides, unsaturated lactones and mixtures of two or more thereof in the presence of hydrogen. More particularly, it relates to the production of $C_4$ to $C_{12}$ ethers optionally co-production of diols and/or the corresponding lactones by the reaction of a feed material comprising di-($C_1$ to $C_4$) alkyl esters of $C_4$ to $C_{12}$ unsaturated dicarboxylic acids and/or anhydrides in the presence of hydrogen. More particularly, it relates to the production of cyclic ethers.

Most particularly, the present invention relates to a process for the production of $C_4$ compounds, more specifically tetrahydrofuran usually with at least some butane-1,4-diol and optionally some γ-butyrolactone, from a hydrocarbon feedstock comprising a maleic acid and/or anhydride or mono and/or di-($C_1$ to $C_4$) alkyl maleate by reaction in a hydrogen rich stream.

It is known to produce diols by reaction of dicarboxylic acids and/or anhydrides, or mono or di- alkyl esters, lactones, and mixtures thereof with hydrogen. Commercially, where the desired product is butane-1,4-diol, typically with the co-products tetrahydrofuran and γ-butyrolactone, the starting material is normally a dialkyl ester of maleic acid and/or anhydride, such as dimethyl maleate or diethyl maleate, which may contain minor amounts of dialkyl fumarate and/or dialkyl succinate.

For further information regarding the operation of these plants reference may be made, for example, to U.S. Pat. Nos. 4,584,419, 4,751,334, WO-A-86/03189, WO-A-88/00937, U.S. Pat. Nos. 4,767,869, 4,945,173, 4,919,765, 5,254,758, 5,310,954 and WO-A-91/01960, the disclosure of each of which is incorporated herein by reference.

The dialkyl maleates which are used as feedstock in these conventional reaction processes may be produced by any suitable means. The production of dialkyl maleates for use in such processes is discussed in detail in U.S. Pat. Nos. 4,584,419, 4,751,334 and WO-A-88/00937. One conventional process for the production of butane-1,4-diol and co-product tetrahydrofuran with optional production of γ-butyrolactone is illustrated schematically in FIG. 1. In this process, a dialkyl ester, such as dimethyl maleate together with any residual methanol from the esterification reactor, is fed via line 1 to a vaporiser 2 where it is vaporised by a stream of hot cycle gas fed to the vaporiser in line 3 which may be mixed with make-up hydrogen fed in line 4. The cycle gas will normally contain a high concentration of hydrogen gas but may also include other gases including hydrocarbons, carbon oxides, methane and nitrogen. Further, where the cycle gas includes recycled gases from downstream, condensables including product ether, methanol, water, co-products and by-products may also be present.

The combined vaporous stream from the vaporiser 2 is then passed in line 5 to the reactor 6 where it is reacted to form butane-1,4-diol, tetrahydrofuran and/or γ-butyrolactone. The product stream 7 is cooled and the reaction products are condensed at 8 and separated from the excess cycle gas before being passed in line 9 to a refining zone 10. In the refining zone 10 the various products are separated and the butane-1,4-diol is removed in line 12 and the tetrahydrofuran in line 13. The γ-butyrolactone, together with the intermediate dimethyl succinate and some butane-1,4-diol may be recycled in lines 14 and 15. In one arrangement the γ-butyrolactone may be at least partially extracted in an optional refining zone (not shown) and recovered. The methanol water stream separated from the product mix will be recycled upstream. In general, a significant portion of the butane-1,4-diol produced by this or other conventional methods is subsequently converted to tetrahydrofuran.

The overall reaction which occurs is a series of steps and includes a final dehydration step in which the tetrahydrofuran is produced. A probable reaction path is set out in Scheme 1.

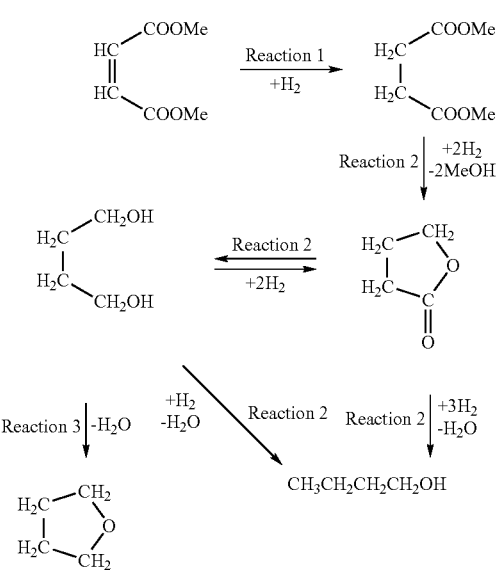

Scheme 1

Reaction 1 may be regarded as hydrogenation (and is a reaction of the carbon/carbon double bond), Reaction 2 may be regarded as hydrogenolysis (and is a reaction of the saturated ester to butanediol, γ-butyrolactone and by-product butanol) and Reaction 3 may be regarded as dehydration (and is a reaction of butanediol to tetrahydrofuran). The above scheme is a likely reaction path.

An alternative process is described in WO-A-99/35113 in which maleic anhydride esters are fed to a reaction process in which three different catalysts are used. First the maleate is converted to the succinate in the presence of the first catalyst which is a heterogeneous selective hydrogenation catalyst at a temperature of from 120° C. to 170° C. and a pressure of 3 to 40 bara. The succinate is then passed directly to the presence of the second catalyst where it is converted mainly into γ-butyrolactone. The product of the reaction with the second catalyst is then fed directly to the presence of a third catalyst which is used to dehydrate the γ-butyrolactone to produce tetrahydrofuran. Some of the γ-butyrolactone formed in the presence of the second catalyst is transferred to a second reaction loop operating at a higher pressure where it is converted to butane-1,4-diol.

As the first step in Scheme 1 and the first catalyst used in the alternative process described in WO-A-99/35113 relates to the hydrogenation of the dimethyl maleate to dimethyl succinate, it has been suggested that dimethyl succinate or diethyl succinate may be suitable starting materials for the reactions with hydrogen to form butane-1,4-diol, tetrahydrofuran and/or γ-butyrolactone. These succinates may be formed by any suitable manner and may be from biotechnology sources.

One process in which dimethyl succinate is used in the production of tetrahydrofuran and butane-1,4-diol is described in U.S. Pat. No. 4,656,297. In this process, methanol is added to the ester feed to increase conversion and reduce transesterification. Another example of a process in which dimethyl succinate is suggested as a feed is WO-A-99/35136 in which reaction with hydrogen occurs over two different catalysts, to form a mixture of tetrahydrofuran and γ-butyrolactone.

Whilst these processes successfully provide the desired products, they do suffer from certain drawbacks and disadvantages. In general these relate to the economics and efficiency of the process. It is therefore an object of the present invention to provide a process which maximise the efficiency of the reaction whilst minimising the cost per unit of product.

In conventional vapour phase reactions with hydrogen the capital and operating costs particularly energy and other utility requirements, are largely determined by the flow rate of the gas fed to the vaporiser which will generally comprise fresh hydrogen and recycled gases from the reactor and is known as the cycle gas. As discussed above, the cycle gas may additionally include other gases. The size of the compressors, heat exchangers and interconnecting pipework is dictated by the cycle gas flow rate as is the power required for compression and the heat required to be added to the reactor feed and removed from the reactor product. There is therefore a strong incentive to minimise the cycle gas flow rate within a particular process.

The quantity of cycle gas required to vaporise a unit amount of feed to a particular process is determined by a number of parameters including the operating pressure, the desired reaction temperature, the vaporiser exit temperature, the vapour pressure of the components to be vaporised, the desired maximum reaction temperature and the temperature rise across the reactor. This means that in a conventional process, if the amount of cycle gas required for the process is to be minimised, as is economically desirable, it will be necessary to maximise the vaporiser exit temperature. However, maintaining a high vaporiser exit temperature means that the reaction temperature must be higher than is generally desired which results in an increase in the formation of undesired by-products which in turn will reduce the efficiency of the reaction and increase the costs per unit product.

It will therefore be understood that the amount of cycle gas required for the reaction is essentially determined by the vaporiser exit temperature and is therefore a compromise between the high temperature required to minimise the cycle gas required to vaporise the feed and the relatively low temperatures required to minimise the production of undesired by-products.

Reactions with hydrogen are often carried out in adiabatic reactors as they are simple to design and construct and can accommodate a large volume of catalyst at lower cost than would be required if a non-adiabatic reactor were to be used. Further benefits of such reactors are that they are generally straightforward to operate and control and do not need complex utility support and control systems. Many reactions with hydrogen are exothermic and therefore where an adiabatic reactor is used there will be a significant temperature rise to the exit. One example of a reaction where this conflict between maximising vaporiser exit temperature and minimising reactor temperature is acute due to the strong exothermic nature of the invention and the use of an adiabatic reactor is the reaction of dialkyl maleate with hydrogen to form tetrahydrofuran, butane-1,4-diol, and γ-butyrolactone. It will be understood that it is generally desirable to minimise reactor temperature as excessive temperature can lead to an increase in the formation of undesirable by-products. By-products are a cause of process inefficiency. In addition they can cause problems with product quality.

It is therefore desirable to provide a process for gas phase reaction with hydrogen in which the cycle gas requirements are minimised such that investment and operating costs are reduced whilst minimising the production of unwanted by-products. It may also be desirable to provide such a process with a high selectivity to the cyclic ether over the diol.

The present invention provides a process which overcomes the disadvantages and drawbacks of the prior art processes and provides a means by which the adiabatic rise across a vapour phase reactor can be reduced to allow the cycle gas loading to be increased for a given exit reactor temperature. As described above, this will offer particular advantages as to efficiency of the process and to product quality.

Thus according to the present invention there is provided a process for the production of an ether optionally with a diol and/or a lactone, by reaction of a corresponding organic feed material selected from unsaturated dicarboxylic acids and/or anhydrides, mono-esters of unsaturated dicarboxylic acids and/or anhydrides, diesters of unsaturated dicarboxylic acids and/or anhydrides, unsaturated lactones, and mixtures of two or more thereof in the presence of hydrogen which comprises the steps of:

(a) supplying a stream comprising at least a portion of the organic feed material to a pre-reactor zone comprising catalyst and operating under reaction conditions and contacting said feed with a hydrogen containing stream such that at least some of the carbon carbon double bonds are saturated;

(b) vaporising the at least partly saturated feed into the hydrogen containing stream in a vaporising zone;

(c) supplying the hydrogen-containing stream containing the vaporised at least partially saturated feed to a reaction zone comprising catalyst and operating under reaction conditions;

(d) recovering from the reaction zone a product stream comprising the ether and optionally diol and/or lactone; and (e) recycling depleted hydrogen-containing stream to at least the pre-reactor zone or the vaporisation zone.

The at least partly saturated feed is preferably vaporised by and into the hydrogen containing stream in step (b).

The pre-reactor zone and the vaporisation zone may be located within the same vessel and may be commingled. In one alternative arrangement, the pre-reactor zone and the vaporisation zone may be located in separate vessels such that the at least partially saturated feed and/or the hydrogen containing stream is recovered from the pre-reactor zone and passed to the vaporisation zone.

The process of the present invention provides a process in which the afore-mentioned disadvantages are overcome and wherein the cycle gas requirements are minimised such that investment and operating costs are reduced and preferably the production of unwanted by-products is minimised which may also contibute to improved product quality.

These advantages may at least in part be achieved if only a fraction of the total feed material for the reaction is subjected to the saturation reaction of step (a). Thus in one embodiment of the present invention in which the pre-reactor zone and the vaporisation zones are separate, additional unsaturated organic feed material may be vaporised into the hydrogen containing stream in step (b) such that the stream supplied to the reaction zone comprises hydrogen, feed material which has not been subjected to reaction in the pre-reactor zone and feed material which has been subjected to hydrogenation reaction in the pre-reactor zone such that at least a portion of the double bonds are saturated. The additional unsaturated organic feed material may, in one arrangement, be vaporised by and into the hydrogen containing stream in step (b).

In another alternative arrangement, feed material which has not been subjected to reaction in the pre-reactor zone may be added to the reaction zone without first being mixed with the stream leaving the pre-reactor zone. In this arrangement, the additional feed material is generally vaporised into, and optionally by, a second hydrogen containing stream.

The pre-reactor zone may be any suitable reactor. In one arrangement, the pre-reactor zone and the vaporiser are combined and may be a liquid and/or vapour phase catalytic vaporiser. In this arrangement, the heat of reaction in the pre-reactor zone may be utilised in the evaporation of some of the liquid feed. In one alternative arrangement, the pre-reactor zone and the vaporiser may be separated and a hydrogen-containing stream, may be fed to both the pre-reactor zone and the vaporiser.

The invention is particularly suitable for a process for the production of tetrahydrofuran, optionally with the co-production of butane-1 4-diol and/or γ-butyrolactone from a feedstock containing a dialkyl maleate (preferably dimethyl maleate) by vapour phase reaction in a hydrogen rich gas. The first step in the reaction process involves the hydrogenation of dimethyl maleate to form dimethyl succinate. This is the most exothermic reaction in the overall synthesis and is responsible for liberating over half of the total heat of reaction from the conversion of dimethyl maleate to tetrahydrofuran. As the vapour pressure of tetrahydrofuran product (8284 mmHg at 165° C.) is significantly higher than that of dimethyl maleate (262 mmHg at 165° C.), dimethyl succinate (328 mmHg at 165° C.) and possible co-products γ-butyrolactone (252 mmHg at 165° C.) and butane-1,4-diol (76 mmHg at 165° C.), the dew point at the reactor exit will be significantly lower than that at the reactor inlet when a significant fraction of the feedstock is converted to tetrahydrofuran.

By using a pre-reaction step to hydrogenate some or all of the dimethyl maleate to dimethyl succinate, the main vapour phase reactor temperature rise can be significantly reduced, such that supplying the feed to the reactor at a higher temperature than is conventionally used does not have the deleterious effects noted heretofore. Thus, as the dimethyl maleate feed in the cycle gas from the vaporisation zone is progressively replaced with dimethyl succinate the temperature from the vaporisation zone can be higher for a given reactor exit temperature, which in turn will lead to an increase in productivity.

An additional benefit is also obtained because the vapour pressure of dimethyl succinate is around 25% higher than that of dimethyl maleate.

The hydrogen-containing stream will normally contain a high concentration of hydrogen but may also include other gases including hydrocarbons, carbon oxides, methane and nitrogen. Further, where the hydrogen containing stream includes recycled gases from downstream, condensables, which may include one or more of product ether, $C_1$ to $C_4$ alkanol, water, co-products and by-products, may also be present By-products may include the alkanol used in the esterification of the acid or anhydride, for example methanol, undesirable material formed in side reactions, for example butanol, water evolved in the dehydration of the diol to the ether together with other light or heavy materials formed in the process.

The by-products may be separated from the desired product in a refining zone and may be further purified if required. Similarly, the co-products may be separated from the desired product in the refining zone and may be further purified if required. However, in one arrangement, one or more of the co-products and/or by-products will be recycled.

The organic feed material is preferably selected from one or more of unsaturated dicarboxylic acids and/or anhydrides, mono $C_1$ to $C_4$ alkyl esters of $C_4$ to $C_{12}$ unsaturated dicarboxylic acids and/or anhydrides, di $C_1$ to $C_4$ alkyl esters of $C_4$ to $C_{12}$ unsaturated dicarboxylic acids and/or anhydrides, lactones of $C_4$ to $C_{12}$ unsaturated hydroxycarboxylic acids, and mixtures of two or more thereof. For example, the organic feed material can be selected from mono $C_1$ to $C_4$ alkyl esters of $C_4$ unsaturated dicarboxylic acids and/or anhydrides, di $C_1$ to $C_4$ alkyl esters of $C_4$ unsaturated dicarboxylic acids and/or anhydrides, and mixtures of two or more thereof. A particularly preferred organic feed material may be selected from monomethyl maleate, monomethyl fumarate, dimethyl maleate, dimethyl fumarate, monoethyl maleate, monoethyl fumarate, diethyl maleate, diethyl fumarate and mixtures of two or more thereof.

Where the feed comprises one or more unsaturated acids and/or anhydrides, the process of the present invention may include an esterification step in which the acid and/or anhydride is converted to a mono- or di-ester. The esterification step, where present, will be carried out in an esterification zone. The esterification zone may be located before or after the pre-reactor zone.

In one arrangement, the organic feed material is contained within an organic solvent. Where the organic solvent is present, the organic feed material may be separated from the organic solvent by hydrogen-containing gas stripping at step (b).

Suitable organic solvents include: di-($C_1$ to $C_4$ alkyl) esters of dicarboxylic acids containing up to 13 carbon atoms; mono- and di-($C_6$ to $C_{18}$ alkyl) esters of maleic acid, fumaric acid, succinic acid and mixtures thereof; ($C_1$ to $C_4$ alkyl) esters of napthalenemonocarboxylic acids; tri-($C_1$ to $C_4$ alkyl) esters of aromatic tricarboxylic acids; di-($C_1$ to $C_4$ alkyl) esters of isophthalic acid; alkyl phthalates; and dimethyl sebecate.

For an arrangement in which the pre-reactor zone and the vaporisation zone are combined, the hydrogen-containing stream:condensable material preferably has a molar ratio in the range of from about 50:1 to about 1000:1. For an arrangement where the pre-reactor zone is separate from the vaporisation zone, the hydrogen-containing stream:condensable material preferably has a molar ratio in the range of from about 1:1 to about 20:1.

Typically the feed temperature to the pre-reactor zone is from about 30° C. to about 250° C., more preferably from about 40° C. to about 200° C., while the feed pressure to the pre-reactor zone is typically from about 5 bara to about 100 bara. The organic feed material is preferably supplied to the pre-reactor zone at a rate corresponding to a liquid hourly space velocity of from about 0.05 to about 20.0 $h^{-1}$ whilst flow rates in the region of about 0.5 to about 5 $h^{-1}$ may be appropriate in some circumstances.

If desired, the pressure and/or the temperature and/or the hydrogen-containing gas:condensable material(s) molar ratio can be adjusted in any convenient manner between the pre-reactor zone and the reactor. The temperature may be adjusted by any suitable means including the use of a heat exchanger or exchangers, for example to obtain a desired degree of superheat above the dewpoint.

The hydrogen containing stream used in the process of the present invention can be obtained by any conventional manner. Preferably it contains at least about 50 volume % up to about 99.99 volume % or more, e.g. from about 80 to about 99.9 volume %, of hydrogen. It may further contain one or more inert gases, such as nitrogen or methane. Conveniently the hydrogen containing stream is produced by pressure swing absorption so that the hydrogen-containing stream molecular weight is minimised thereby reducing the power required for compression and circulation of the gaseous streams.

Any suitable catalyst for the reaction may be selected. Whilst a mixture of catalysts may be used, for ease of reference the term "catalyst" will be used herein and will be understood to mean either a single catalyst or a mixture of two or more different catalysts. The catalyst used in the reactor may be different from that used in the pre-reactor zone. In the pre-reactor zone, a catalyst which is selective to the hydrogenation of carbon carbon double bonds, but with little or no selectivity to ester hydrogenolysis is preferably used.

The choice of catalyst may also be influenced by the phase or phases in which reaction is to occur. It may, in one arrangement such as when the reaction occurs in the liquid or gas/liquid phase, be desirable to deliberately reduce the activity of the catalyst in order to reduce the ester hydrogenolysis characteristics. This is because in some circumstances, the formation of the diol may result in reaction with the feed material to form polymers.

Examples of suitable catalysts for use in the pre-reactor zone include nickel, palladium, ruthenium and cobalt hydrogenation catalysts, copper chromite, copper oxide, zinc oxide and copper oxide/zinc oxide mixture. These catalysts may be used alone or in combination.

Where the pre-reactor zone and the vaporisation zone are commingled, the catalyst may act as the surface on which vaporisation occurs. In this arrangement, the choice of catalyst may also take into consideration the catalyst shape and/or its packing.

In one arrangement, the catalyst for the reaction zone may be a bed comprising a variety of catalysts. In one example, the bed may include a catalyst that is tolerant of residual feed acid content, one which is suitable to promote hydrogenation of the ester and another which promotes selectivity to the desired product, preferably the ether. Catalyst beds comprising more than one type of catalyst may comprise discrete layers of catalyst within the bed such that different types are separated or the different catalyst types may be admixed.

In a particularly preferred process the catalyst of the reactor is selected from copper-containing catalysts, such as a reduced copper chromite catalyst or a reduced copper containing catalyst. Examples of copper-containing catalysts include reduced copper oxide/zinc oxide catalysts, reduced manganese promoted copper catalysts, reduced copper chromite catalysts, and reduced promoted copper chromite catalysts. One alternative catalyst for use in the reactor is a reduced manganese promoted copper catalyst.

Where the catalyst is a copper-containing catalyst, the active catalytic species may be at least partially supported on a supporting material which may be selected from chromia, zinc oxide, alumina, silica, silica-alumina, silicon carbide, zirconia, titania, carbon, or a mixture of two or more thereof, for example, a mixture of chromia and carbon.

In one preferred process of the present invention an acid tolerant catalyst such as a promoted copper chromite catalyst may be used in the reactor. A suitable promoted copper chromite catalyst is, for example, the catalyst sold as PG85/1 by Davy Process Technology Limited of The Technology Centre, Princeton Drive, Thornaby, Stockton-on-Tees, TS 17 6PY, England.

A catalyst which is effective to react the ester to diols and lactones such as a manganese promoted copper catalyst may also be used in the reactor. A suitable manganese promoted copper catalyst which exhibits superior conversion of a dialkyl ester under typical operating conditions used for catalyst PG85/1 is sold as DRD92/89A by Davy Process Technology Limited. An example of a catalyst with a high selectivity to the desired ether under typical operating conditions is DRD92/89B which is also available from Davy Process Technology Limited.

Further details of suitable catalysts for use in the production of butane-1,4-diol, γ-butyrolactone and/or tetrahydrofuran can be found in International Patent Application No. PCT/GB00/04758 which is incorporated herein by reference.

The amount of hydrogenation catalyst used in the pre-reactor zone and the amount of hydrogenation/hydrogenolysis catalyst in the reactor may be the same or different. In a preferred arrangement, the amount of hydrogenation catalyst used in the pre-reactor zone will be less than the amount of hydrogenation/hydrogenolysis catalyst used in the reaction zone. The catalyst charge in the pre-reactor zone may constitute from about 1% to about 30%, more usually about 3% to about 15%, of the total hydrogenation/hydrogenolysis catalyst volume in the reaction zones.

In the reaction to convert an ester to an ether, the reactor will also contain some dehydration catalyst to produce higher quantities of the desired ether, preferably a cyclic ether which may be tetrahydrofuran. The hydrogenation/hydrogenolysis catalyst, such as PG 95/1 and/or DRD 92/89A will typically produce up to about 10% ether although more may be achieved if the temperature and/or the residence time is elevated. The dehydration catalyst such as DRD 92/89B, which may also contribute some hydrogenation/hydrogenolysis, allows the ether level to be raised up to 90% or more depending on the amount of the catalyst. In a preferred arrangement an amount of ether of about 30% or more may be achieved. These catalysts are particularly suitable for the production of tetrahydrofuran.

The product stream from the reactor is preferably fed, preferably having been condensed, to a refining zone where the desired ether, preferably tetrahydrofuran, is separated as product. Any co-products, such as butane-1,4-diol and/or γ-butyrolactone, which may be present may be separated or may be recycled to the reaction system. The recycle may be to any suitable point in the process. In one arrangement, the recycle may be vaporised into, and preferably by, the hydrogen containing stream at step (b). In one alternative arrangement, the recycle may be vaporised into, and preferably by, a second hydrogen-containing stream before being supplied to the reaction zone in step (c). Where there is more than one co-product, one or more may be separated and recovered and the remainder recycled.

In one arrangement where 100% conversion to ether, for example tetrahydrofuran, is desired all of the co-products, for example butane-1,4-diol and/or γ-butyrolactone, are recycled.

The ability to select suitable catalysts and adjust the recycling of co-products to the vaporisation zone allows the plant operator flexibility to select the amount of ether produced relative to the formation of co-products.

In one arrangement, the dehydration catalyst may be provided in a manner which allows the operator to choose to have at least some of the reactants bypass the catalyst. This allows the ether produced to be varied.

Any alkanol derived from the organic feed, which will typically be a $C_1$ to $C_4$ alkanol, and water in the crude product stream will preferably be condensed and separated in refining. The alkanol will conventionally be recycled to the esterification reactor in which the organic feed material is formed, if present. The refining system may include means, if required to separate the water from the alkanol. The refining system will usually include means to separate other by-products which may be recycled. An example of a by-product which may be recycled is, for example, any intermediate material. Alternatively some or all of any by-products produced may be rejected as effluent. An example of a by-product which may be rejected is any mono-ol produced.

The present invention will now be described, by way of example, with reference to the accompanying drawings in which.

It will be understood by those skilled in the art that the drawings are diagrammatic and that further items of equipment such as reflux drums, pumps, vacuum pumps, compressors, gas recycle compressors, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

The present invention will now be described with particular reference to the production of tetrahydrofuran by reaction of a feed of dimethyl maleate with hydrogen.

Figure 2:
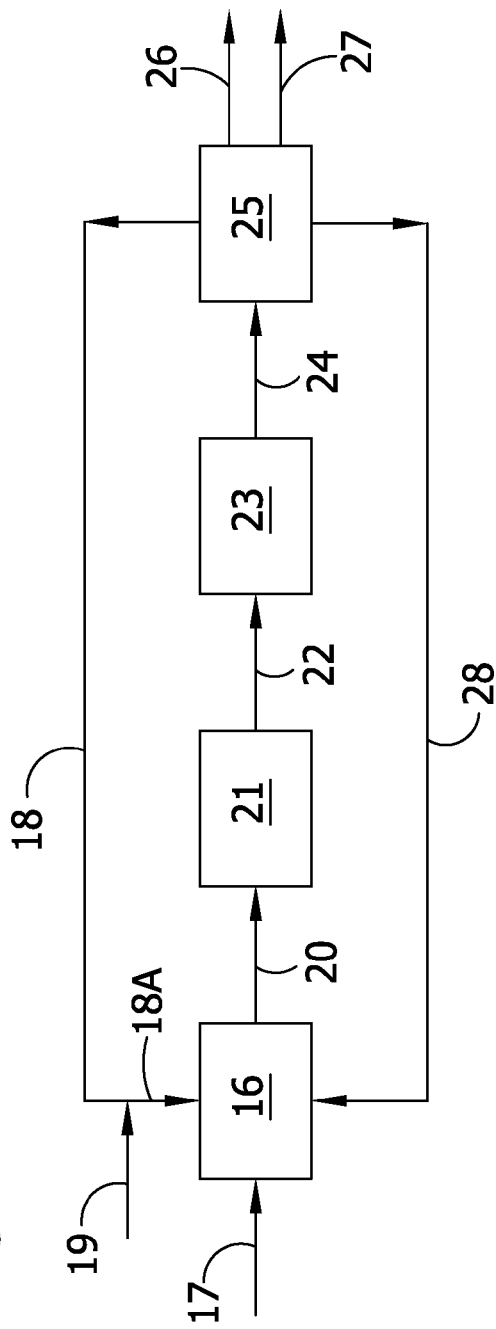
FIG. 2 is a schematic diagram of a process in accordance with one embodiment of the present invention.

FIG. 2 illustrates a plant for the production of tetrahydrofuran by reaction of dimethyl maleate with hydrogen in accordance with one embodiment of the present invention. The dimethyl maleate may be produced by any suitable means and may be supplied from an esterification plant (not shown) of the type described in WO-A-90/08127 which is incorporated herein by reference.

The resulting dimethyl maleate typically contains no more than about 10.0 wt/wt % of acidic organic materials, such as monomethyl maleate, and preferably less than about 2.0 wt/wt %, e.g. about 0.1 to about 1.0 wt/wt %, of acidic materials.

In the arrangement of FIG. 2, the pre-reactor zone and the vaporiser zone are combined into a vaporiser and pre-hydrogenation reactor 16. The dimethyl maleate is fed to this vaporiser and pre-reaction zone at line 17. The pre-reactor zone comprises a suitable hydrogenation catalyst. In the pre-reaction zone at least some and preferably the majority of the feed is reacted to form dimethyl succinate and vaporised against hydrogen-containing stream fed in line 18a which may be a combination of depleted hydrogen-containing stream from line 18 combined with make-up hydrogen from line 19. The dimethyl succinate which is vaporised into the hydrogen-containing stream is passed in line 20 to the reaction-zone 21, where further reaction is carried out over a suitable catalyst.

The catalyst charge preferably contains acid tolerant catalyst such as PG85/1 and DRD92/89A which promote ester hydrogenation and, for example, DRD 92/89B which promotes diol dehydration. Conversion of dimethyl maleate to tetrahydrofuran, butane-1,4-diol and γ-butyrolactone, as well as small quantities of undesirable by-products, such as butanol and/or acetal 2-(4'-hydroxybutoxy)-tetrahydrofuran, occurs in passage through reactor 21.

The product stream 22 is passed to a cooler and condenser 23 where the crude product is separated form the cycle gas which is recycled via a line 18 to a compressor (not shown) and line 18 and 18a to the vaporiser 16.

Crude product is passed in line 24 to a refining zone 25. Here the crude product stream is separated, preferably by distillation in several stages, to yield essentially pure tetrahydrofuran which is recovered in line 26. Line 27 for the recovery of the butane-1,4-diol may be provided or in one alternative arrangement, this may be recycled to the combined pre-reactor zone/vaporisation zone 16 for further reaction to yield tetrahydrofuran. Any γ-butyrolactone together with partially hydrogenated fed material may be recycled in line 28 to the combined pre-reactor zone/vaporisation zone 16. Alternatively, the γ-butyrolactone may be refined and recovered as a separate product. Methanol and water may be recycled to up-stream reactors or may be separated and the methanol recycled and the water extracted as effluent.

Figure 3:
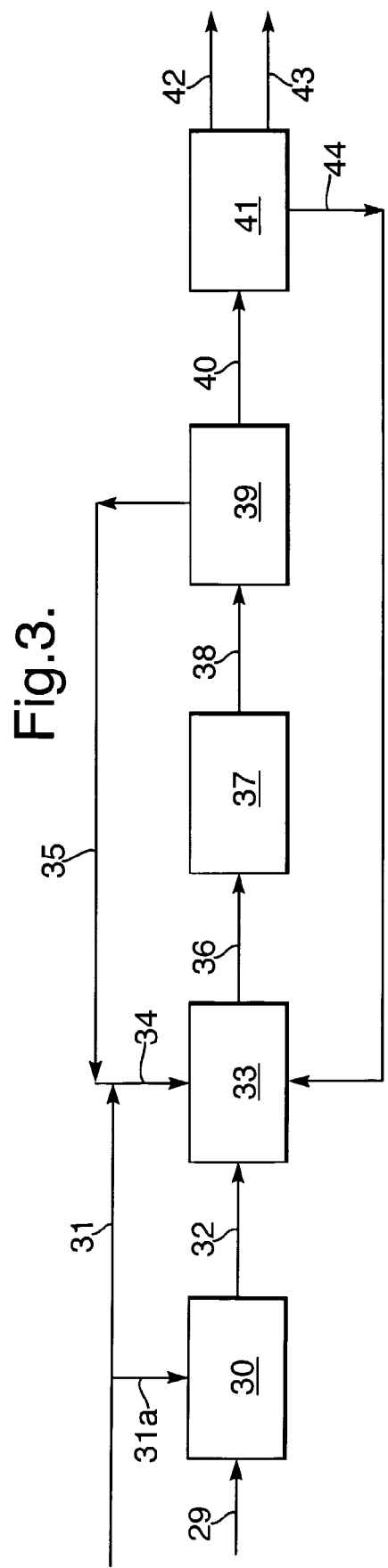
FIG. 3 is a schematic diagram of a process in accordance with a second embodiment of the present invention.

With reference to FIG. 3 an alternative arrangement for the present invention will now be described. In this arrangement, the dimethyl maleate is fed in line 29 to a pre-reactor zone 30 where it is subjected to hydrogenation in the liquid phase with hydrogen from line 31a in the presence of a suitable hydrogenation catalyst.

The resultant dimethyl succinate rich stream is then passed in line 32 to a vaporiser 33. The dimethyl succinate may be pumped to near the top of the vaporisation zone. The feed flows down the vaporisation zone against an up-flowing stream of cycle gas from line 34 which may include fresh make up hydrogen fed from line 31 that has been added to recycled hydrogen-containing stream (line 35) from downstream. Alternatively, it may simply be the recovered hydrogen-containing stream from line 35 and any makeup hydrogen may be added directly to any suitable point in the hydrogenation loop.

A near saturated vapour mixture stream comprising dimethyl succinate in hydrogen-containing stream, with a hydrogen-containing stream:dimethyl succinate molar ratio of about 50:1 to about 1000:1 is recovered from the top of the vaporisation zone 33.

The mixture of gases is then fed in line 36 to the reactor 37 which contains a fixed bed catalyst charge.

The hydrogenolysis and dehydration catalysts will be the same as those described in connection with FIG. 2. The reaction zone is typically operated at an inlet temperature of from about 100° C. to about 300° C., more preferably of from about 150° C. to about 250° C., an inlet pressure of from about 5 bara to about 150 bara, more preferably from about 30 bara to about 70 bara. The dimethyl succinate feed rate preferably corresponds to a liquid hourly space velocity of from about $0.5\ h^{-1}$ to about $5.0\ h^{-1}$. Conversion of dimethyl maleate to tetrahydrofuran, butane-1,4-diol and γ-butyrolactone, as well as small quantities of undesirable by-products, such as butanol and/or acetal 2-(4'-hydroxybutoxy)-tetrahydrofuran, occurs in passage through reactor 37.

The product stream 38 is passed to a cooler and condenser 39 where the crude product is separated from the depleted hydrogen-containing stream which is recycled via a line 35 to a compressor (not shown) and line 35 to the vaporisation zone 33.

Crude product is passed in line 40 to a separating system 41. Here the crude product stream is separated, preferably by distillation in several stages, to yield pure tetrahydrofuran which is recovered in line 42. Line 43 for the recovery of the butane-1,4-diol may be provided or in one alternative arrangement, this may be recycled to the vaporisation zone 33 for further reaction to yield tetrahydrofuran. Any γ-butyrolactone together with partially hydrogenated feed material may be recycled in line 33 to the vaporisation zone 44. Alternatively, γ-butyrolactone may be refined as a product.

Methanol and water may be recycled to upstream reactors or may be separated and the methanol recycled and the water extracted as effluent.

With reference to FIG. 3, an alternative arrangement for the present invention will now be described The invention will now be further described with reference to the accompanying examples.

COMPARATIVE EXAMPLE 1

Figure 1:
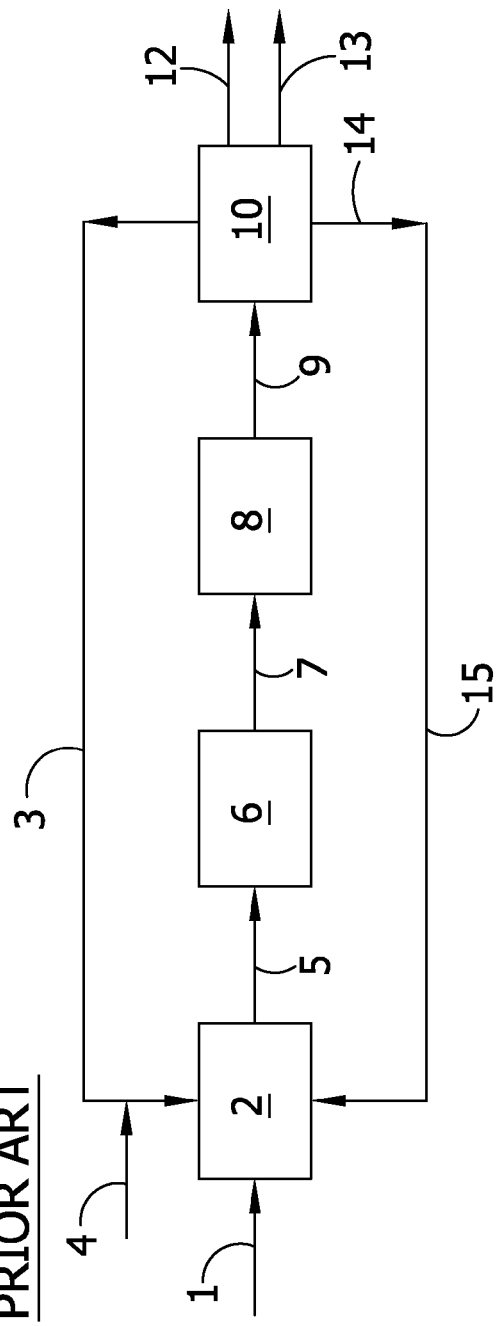
FIG. 1 is a schematic diagram of a prior art arrangement.

In a prior art process as illustrated in FIG. 1, in order to vaporise 1.0 kmol/h of dimethyl maleate which is fed to the vaporiser, along with 0.21 kmol/h of refining recycle, 258 kmols/h of hydrogen rich cycle gas and 5.0 kmol/h of make up hydrogen are also fed to the vaporiser. The vaporised stream is then fed to the reactor where the dimethyl maleate and refining recycles are converted to crude reaction product. These are cooled and separated and the crude product fed to a refining zone where the products are refined and the refining recycles returned to the vaporiser. The details and results are set our in Table 1.

Example 1

In a process scheme in accordance with the present invention and as illustrated in FIG. 2 the compressor cycle gas stream is maintained at the same absolute rate as that for Comparative Example 1. In this arrangement 1.32 kmol/h of dimethyl maleate is fed to the lower vaporisation section of a combined pre-reactor zone/vaporisation zone. In addition, 258 kmols/h of hydrogen rich cycle gas and 8.3 kmol/h of make up hydrogen are also fed to the vaporisation zone. The dimethyl maleate feed is vaporised into the hydrogen stream and then passes over a supported palladium catalyst at 167° C. where it is converted to dimethyl succinate. The remaining 0.33 kmolh$^{-1}$ of dimethyl maleate along with 0.35 kmol$^{-1}$ of recycled material from the refining zone is vaporised into the dimethyl succinate containing hydrogen stream in a second vaporisation section, utilising the heat generated from the formation of the dimethyl succinate to provide heat for the vaporisation.

By sending a predominately dimethyl succinate stream rather than a dimethyl maleate feedstock to the vapour phase hydrogenation reactor, the vapour phase hydrogenation reactor inlet temperature can be raised by around 9° C., whilst maintaining a constant reactor outlet temperature of 195° C. It can be seen that approximately 65% more dimethyl maleate is processed than is possible with the procedure of Comparative Example 1.

Example 2

In a process scheme in accordance with the present invention and as illustrated in FIG. 3 the compressor cycle gas stream is maintained at the same absolute rate as that for Comparative Example 1. In this arrangement 1.84 kmol/h of dimethyl maleate is first pre-hydrogenated to dimethyl succinate in the liquid phase over a nickel based catalyst at 60° C. and 12 bara, prior to feeding the dimethyl succinate along with 0.39 kmol/h of refining recycle to the vaporiser. A hydrogen feed of 2.2 kmol/h is fed to the pre-hydrogenation section. In addition, 258 kmols/h of hydrogen rich cycle gas and 7.4 kmol/h of make up hydrogen are also fed to the vaporiser. By sending a predominantly dimethyl succinate rather than a dimethyl maleate feedstock to the vaporiser, the vapour phase hydrogenation reactor inlet temperature can be raised by around 13° C., whilst maintaining a constant reactor outlet temperature of 195° C. It can be seen that approximately 84% more dimethyl maleate is processed than is possible with the procedure of Comparative Example 1.

The process of the present invention may be used in combination with the process of WO03/006446 the contents of which are incorporated herein by reference.

TABLE 1

|  |  | Comparative. Example 1 | Example 1 | Example 2 |
| --- | --- | --- | --- | --- |
| Dimethyl maleate Feed | kmol/h | 1.0 | 1.65 | 1.84 |
| Refining Recycle | kmol/h | 0.21 | 0.35 | 0.39 |
| Increase in dimethyl maleate processed compared to Comp. Example 1 | % | N/A | 65 | 84 |
| Reactor inlet temperature | ° C. | 170 | 179 | 183 |
| Gas Loop Make up Hydrogen | kmol/h | 5.0 | 8.3 | 7.4 |
| Pre-hydrogenation Make up Hydrogen | kmol/h | N/A | N/A | 2.2 |
| Cycle gas at compressor | kmol/h | 258 | 258 | 258 |
| Cycle gas/dimethyl maleate feed | kmol/kmol | 258 | 157 | 140 |
| Reactor Exit Pressure | bara | 62.8 | 62.8 | 62.8 |
| Reactor Exit Temperature | ° C. | 195 | 195 | 195 |

The invention claimed is:

1. A process for the production of an ether optionally with a diol and/or a lactone, by reaction of a corresponding organic feed material selected from mono $C_1$ to $C_4$ alkyl esters of $C_4$ to $C_{12}$ unsaturated dicarboxylic acids and/or anhydrides, di-($C_1$ to $C_4$) alkyl esters of $C_4$ to $C_{12}$ unsaturated dicarboxylic acids and/or anhydrides, lactones of $C_4$ to $C_{12}$ unsaturated hydroxycarboxylic acids, and mixtures of two or more thereof in the presence of hydrogen which comprises the steps of:
   (a) supplying a stream comprising at least a portion of the organic feed material to a pre-reactor zone comprising catalyst and contacting said feed with a hydrogen containing stream in the pre-reactor zone such that at least some of the carbon carbon double bonds are saturated, wherein the at least partial carbon double bond saturation occurs in a liquid phase in the pre-reactor zone;
   (b) vaporising the at least partly saturated feed into the hydrogen containing stream in a vaporising zone;
   (c) supplying the hydrogen-containing stream containing the vaporised at least partially saturated feed to a reaction zone comprising catalyst;
   (d) recovering from the reaction zone a product stream comprising the ether and optionally diol and/or lactone; and
   (e) recycling a depleted hydrogen-containing stream to at least the pre-reactor zone or the vaporisation zone.

2. A process according to claim 1 wherein the at least partly saturated feed is vaporised by and into the hydrogen in step (b).

3. A process according to claim 1 wherein the pre-reactor zone and vaporisation zone are separate zones within the same vessel.

4. A process according to claim 1 wherein the pre-reactor zone and vaporisation zone are commingled.

5. A process according to claim 4 wherein the catalyst in the pre-reactor zone provides a contact area on which vaporisation occurs.

6. A process according to claim 1 wherein the pre-reactor zone and the vaporisation zone are located in separate vessels such that the at least partially saturated feed from the pre-reactor zone is passed to the vaporisation zone.

7. A process according to claim 1 wherein additional unsaturated organic feed material is vaporised into the hydrogen-containing stream in the vaporisation zone.

8. A process according to claim 7 wherein the additional unsaturated organic feed material is vaporised by the hydrogen containing stream.

9. A process according to claim 1 wherein additional unsaturated organic feed material is supplied to the reaction zone in step (c).

10. A process according to claim 9 wherein the additional unsaturated organic feed material is vaporised into a second hydrogen-containing stream before being supplied to the reaction zone in step (c).

11. A process according to claim 10 wherein the additional unsaturated organic feed material is vaporised by the second hydrogen containing stream.

12. A process according to claim 1 wherein unreacted feed material and by-products, which may optionally include the diol and/or lactone, are recycled and are vaporised into a hydrogen-containing stream in a vaporisation zone.

13. A process according to claim 12 wherein the recycled stream is vaporised by the hydrogen containing stream.

14. A process according to claim 1 wherein unreacted feed material and by-products, which may optionally include the diol and/or lactone, are recycled and are vaporised into a second hydrogen-containing stream before being supplied to the reaction zone in step (c).

15. A process according to claim 14 wherein the recycled stream is vaporised by the second hydrogen containing stream.

16. A process according to claim 1 wherein the feed material is contained within an organic solvent which is separated from the feed material in either the vaporisation zone or in a separate stripping column by cycle gas stripping.

17. A process according to claim 1 wherein the organic feed material is selected from monomethyl maleate, monomethyl fumarate, dimethyl maleate, dimethyl fumarate, monoethyl maleate, monoethyl fumarate, diethyl maleate, diethyl fumarate and mixtures of two or more thereof.

18. A process according to claim 1 wherein the feed is one or more unsaturated acids and/or anhydrides and the process includes an esterification step.

19. A process according to claim 18 wherein the esterification step is carried out in an esterification zone.

20. A process according to claim 19 wherein the esterification zone is located before or after the pre-reactor zone.

21. A process according to claim 1 wherein the ether is tetrahydrofuran.

\* \* \* \* \*